US007712940B2

(12) United States Patent
Ogawa (10) Patent No.: US 7,712,940 B2
(45) Date of Patent: May 11, 2010

(54) LIGHT SOURCE UNIT (75) Inventor: Tomoaki Ogawa, Machida (JP)

(73) Assignee: Olympus Medical Systems Corp. (JP)

( * ) Notice: Subject to any disclaimer, the term of this patent is extended or adjusted under 35 U.S.C. 154(b) by 29 days.

(21) Appl. No.: 12/241,110

(22) Filed: Sep. 30, 2008

(65) Prior Publication Data
US 2009/0122574 A1 May 14, 2009

(30) Foreign Application Priority Data
Nov. 13, 2007 (JP) ............... 2007-294709

(51) Int. Cl.
*A61B 1/06* (2006.01)
(52) U.S. Cl. ................. 362/572; 362/574; 362/555; 362/577
(58) Field of Classification Search ......... 362/572, 362/574, 581, 555, 577, 109; 600/131, 101
See application file for complete search history.

(56) References Cited
U.S. PATENT DOCUMENTS

2006/0126080 A1* 6/2006 Kusuzawa .............. 356/635

2006/0129041 A1* 6/2006 Ellis et al. .............. 600/341
2008/0018734 A1* 1/2008 Iriyama .................. 348/72

FOREIGN PATENT DOCUMENTS

JP 2005-211204 8/2005

* cited by examiner

*Primary Examiner*—Ali Alavi
(74) *Attorney, Agent, or Firm*—Ostrolenk Faber LLP (57) ABSTRACT A light source unit includes a light source including a light emitting portion, a light source holding member holding the light source, a light transmission member including an incident portion wherein light from the light emitting portion is to enter the incident portion, a light transmission member holding member holding the light transmission member, a positioning portion provided on the light transmission member holding member and abutted on the light source to position the light transmission member holding member and the light source to position the incident portion and the light emitting portion, and an adjustment joining mechanism configured to join the light transmission member holding member and the light source holding member to each other so as to adjust the relative positions thereof, and joining them to each other in a state where the light source and the positioning portion abut on each other.

12 Claims, 5 Drawing Sheets

LIGHT SOURCE UNIT

CROSS-REFERENCE TO RELATED APPLICATIONS

This application is based upon and claims the benefit of priority from prior Japanese Patent Application No. 2007-294709, filed Nov. 13, 2007, the entire contents of which are incorporated herein by reference.

BACKGROUND OF THE INVENTION

1. Field of the Invention

The present invention relates to a light source unit wherein light from a light emitting portion of a light source is to enter an incident portion of a light transmission member.

2. Description of the Related Art

Various light source units have been used, wherein light from a light emitting portion of a light source is to enter an incident portion of a light transmission member.

In Jpn. Pat. Appln. KOKAI Publication No. 2005-211204, a portable endoscope is disclosed, the portable endoscope including a light source device as the light source unit. That is, in the portable endoscope, the proximal end of an elongated insertion portion to be inserted into a body cavity is connected to an operating portion to be held and operated by an operator, and the small-sized light source device is attached to the operating portion. In the light source device, illuminative light from a light source lamp enters the proximal end surface of a light guide via a collector lens. The light guide is inserted through the operating portion and the insertion portion to extend to the distal end of the insertion portion, and the illuminative light guided by the light guide is emitted from the distal end surface of the light guide to irradiate an observation target from the distal end of the insertion portion.

BRIEF SUMMARY OF THE INVENTION

In an aspect of the present invention, a light source unit includes: a light source including a light emitting portion; a light source holding member holding the light source; a light transmission member including an incident portion wherein light from the light emitting portion is to enter the incident portion; a light transmission member holding member holding the light transmission member; a positioning portion provided on the light transmission member holding member and abutted on the light source to position the light transmission member holding member and the light source to position the incident portion and the light emitting portion; and an adjustment joining mechanism configured to join the light transmission member holding member and the light source holding member to each other so as to adjust the relative positions of the light transmission member holding member and the light source holding member, and joining the light transmission member holding member and the light source holding member to each other in a state where the light source and the positioning portion abut on each other.

In another aspect of the present invention, an endoscope includes a light source unit and the light source unit includes: a light source including a light emitting portion; a light source holding member holding the light source; a light transmission member including an incident portion wherein light from the light emitting portion is to enter the incident portion; a light transmission member holding member holding the light transmission member; a positioning portion provided on the light transmission member holding member and abutted on the light source to position the light transmission member holding member and the light source to position the incident portion and the light emitting portion; and an adjustment joining mechanism configured to join the light transmission member holding member and the light source holding member to each other so as to adjust the relative positions of the light transmission member holding member and the light source holding member, and joining the light transmission member holding member and the light source holding member to each other in a state where the light source and the positioning portion abut on each other.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, an embodiment of the present invention will be described with reference to the drawings.

FIGS. 1 to 7 show the embodiment of the present invention.

Figure 1:
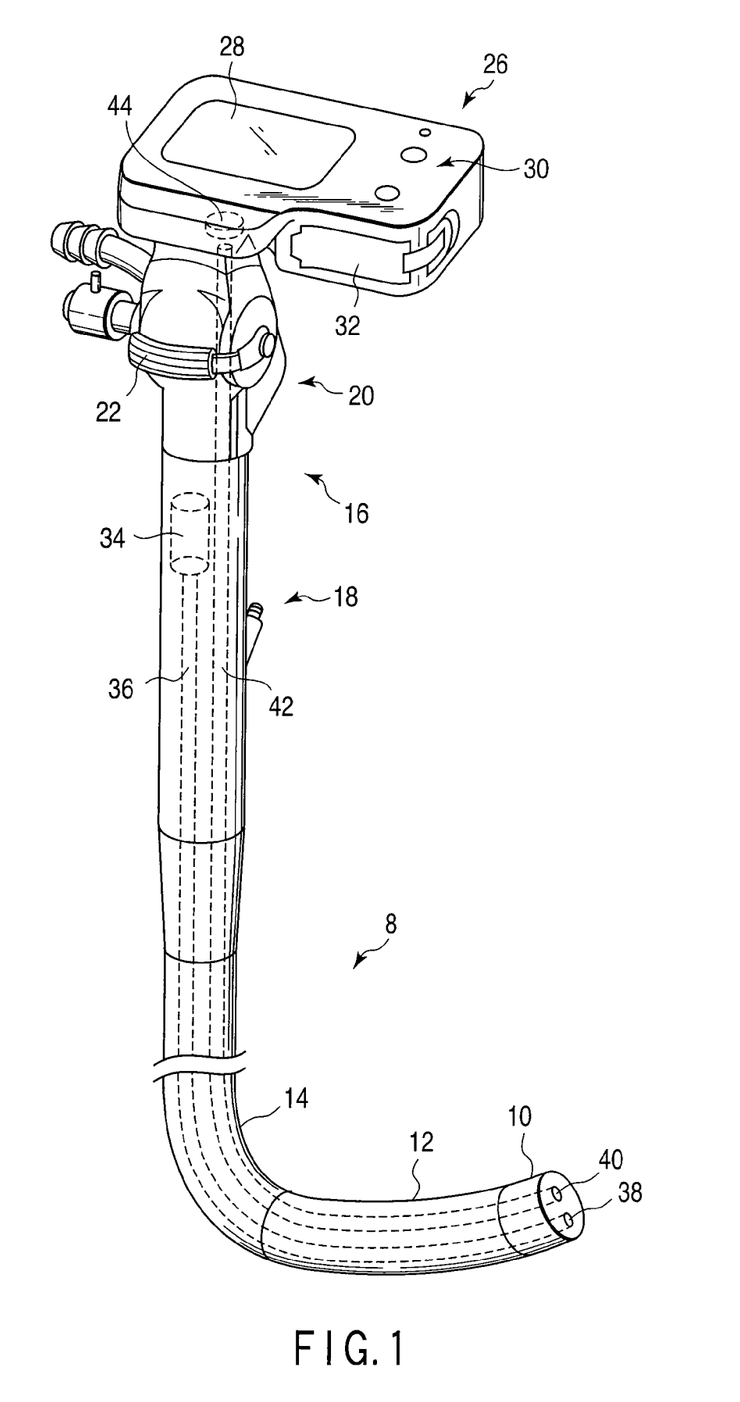
FIG. 1 is a perspective view showing an endoscope of an embodiment of the present invention.

As shown in FIG. 1, a portable endoscope of the present embodiment includes an elongated insertion portion 8 to be inserted into a body cavity. In the insertion portion 8, a distal end rigid portion 10 having rigidity, a bending portion 12 to be operated to be bent, and an insertion tube portion 14 being elongated and having flexibility are arranged from a distal end side to a proximal end side. The proximal end portion of the insertion portion 8 is connected to an operating portion 16 to be grasped and operated by an operator. The operating portion 16 is formed of a distal end side grasping portion 18 and a proximal end side operating portion main body 20.

An LED unit 34 as a light source unit to generate illuminative light is built in the grasping portion 18. One end portion of a light guide 36 as a light transmission member is connected to the LED unit 34. The light guide 36 is inserted through the operating portion 16 and the insertion portion 8 to be extended to the distal end rigid portion 10 of the insertion portion 8. In the distal end rigid portion 10, the distal end portion of the light guide 36 is connected to an illumination optical system, and an illumination window 38 is arranged on the distal end side of the illumination optical system. The illuminative light generated by the LED unit 34 is guided by the light guide 36 to irradiate an observation target from the illumination window 38 via the illumination optical system. On the other hand, in the distal end rigid portion 10, an observation optical system is arranged on the proximal end side of an observation window 40, and the distal end portion of an image guide 42 is connected to the observation optical system. The image guide 42 is inserted through the insertion portion 8 and the operating portion 16 to be extended to the operating portion main body 20. In the operating portion main body 20, the proximal end portion of the image guide 42 is connected to an image pickup unit 44. An observation image is formed on the distal end surface of the image guide 42 by the observation optical system via the observation window 40, transmitted by the image guide 42 and picked by the image pickup unit 44.

A display device 26 to display the observation image picked by the image pickup unit 44 is connected to the operating portion main body 20. The display device 26 is provided with a monitor 28 to display the observation image and a changeover switch 30 to switch the observation image to be recorded between a dynamic image and a static image. Moreover, the display device 26 is provided with a battery as a power source for the whole portable endoscope, and a storage portion 32 to receive a recording medium for recording the image.

In addition, the operating portion main body 20 is provided with a switch to record or reproduce the observation image, a bending operation lever 22 to make the bending portion 12 to be operated to be bent, and the like.

The LED unit 34 will be described with reference to FIGS. 2 to 6.

A positioning mechanism in the LED unit 34 will hereinafter be described.

Figure 2:
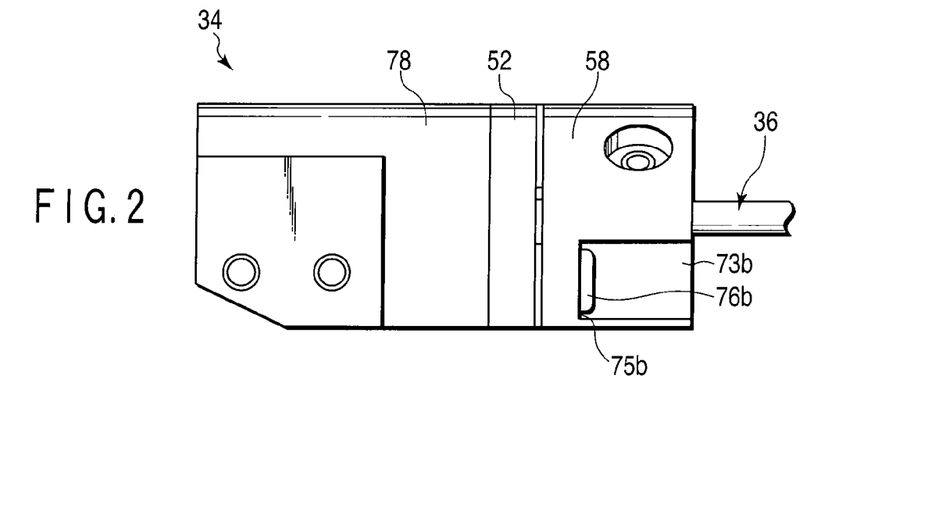
FIG. 2 is a side view showing a LED unit of the embodiment of the present invention.
Figure 3A:
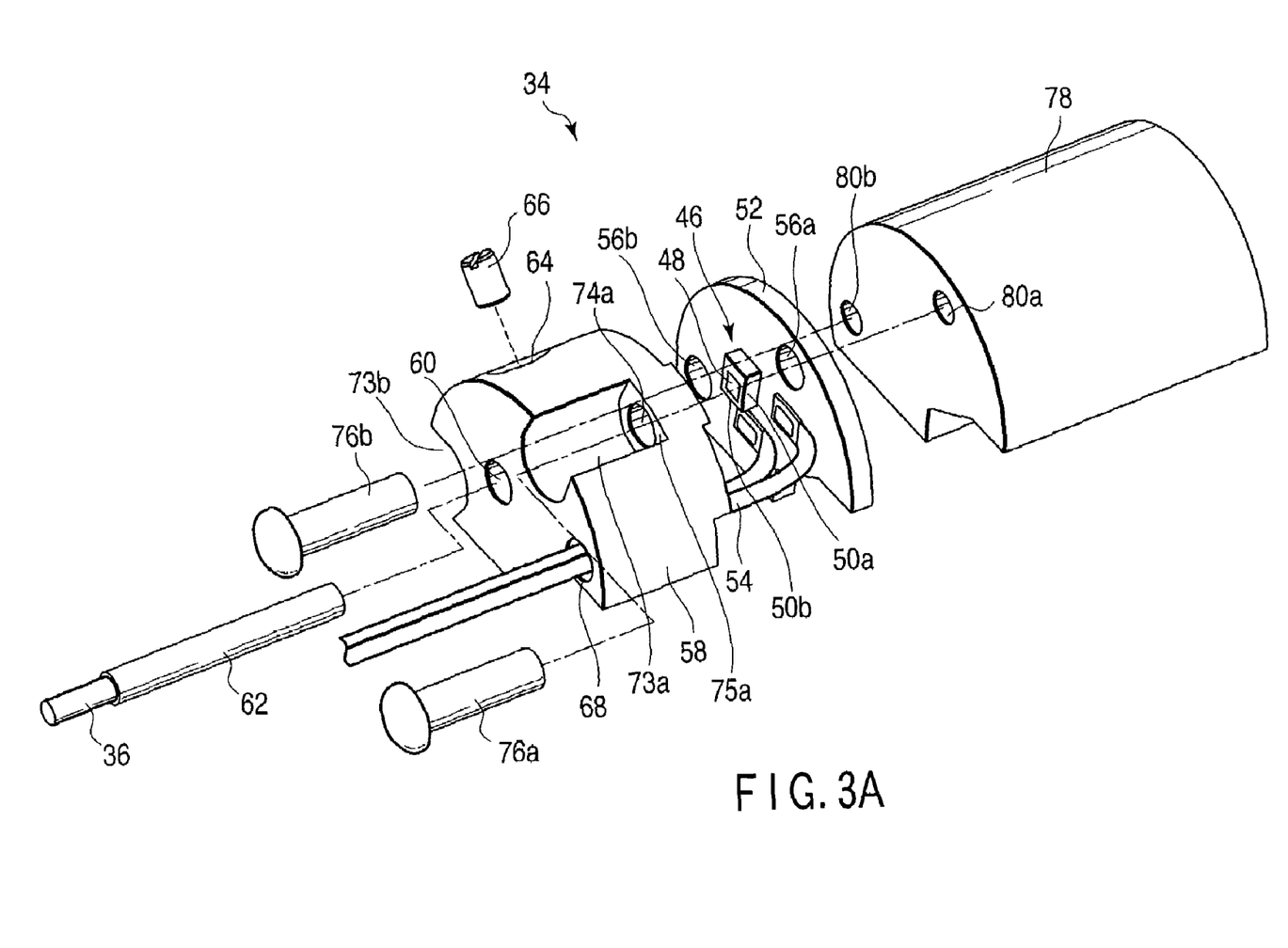
FIG. 3A is an exploded perspective view showing the LED unit of the embodiment of the present invention.
Figure 3B:
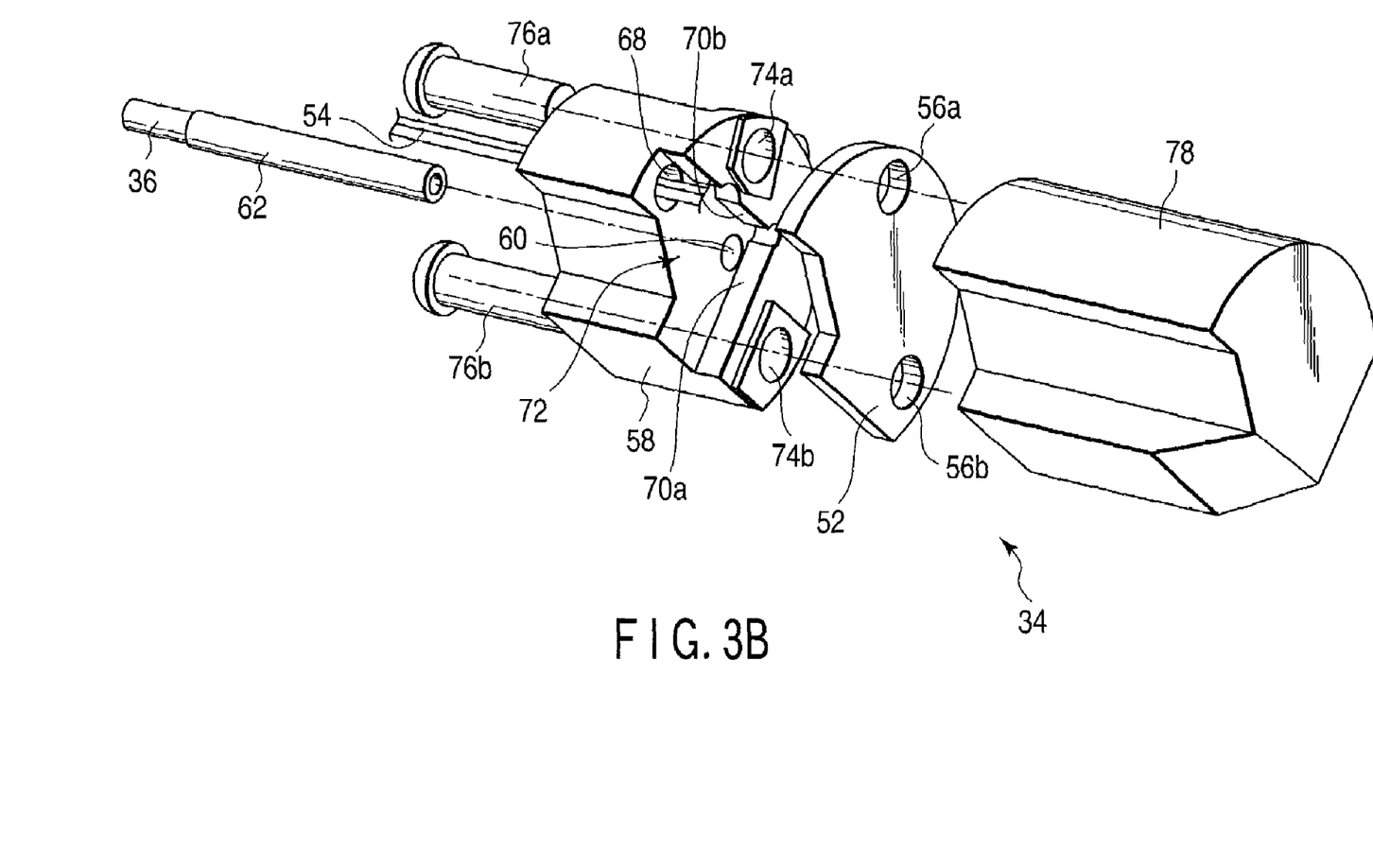
FIG. 3B is another exploded perspective view showing the LED unit of the embodiment of the present invention.

As shown in FIGS. 2, 3A and 3B, in the LED unit 34, an LED 46 as a light source is mounted on an LED substrate 52 as a light source holding member. Here, in the LED substrate 52, the surface on which the LED 46 is mounted is referred to as a mounting surface, and the surface opposite to the mounting surface is referred to as a back surface. The LED 46 has a rectangular parallelepiped shape, and includes a bottom surface, a top surface and first to fourth side surfaces. The LED substrate 52 is arranged on the bottom surface side of the LED 46. A square light emission surface 48 as a light emitting portion is arranged on the top surface of the LED 46. Among the first to fourth side surfaces of the LED 46, the first and second side surfaces 50a, 50b adjacent to each other are used for positioning. Here, the light emitting direction of the LED 46 is substantially orthogonal to the LED substrate 52, and the normal directions of the first and second side surfaces 50a, 50b are substantially orthogonal to the light emitting direction of the LED 46.

A light guide holding member 58 as a light transmission member holding member is arranged on the mounting surface side of the LED substrate 52. The light guide holding member 58 has a substantially columnar shape, and the axial direction thereof is substantially orthogonal to the LED substrate 52. Here, a light guide connecter 62 is fitted over the proximal end portion of the light guide 36. A light guide insertion hole 60 through which the light guide connecter 62 is to be inserted is formed in the axial direction through the light guide holding member 58. A fixing screw hole 64 is bored from the outer peripheral surface of the light guide holding member 58 to the light guide insertion hole 60, and screwing a fixing screw 66 into the fixing screw hole 64 enables fixing of the light guide connecter 62 to the light guide holding member 58.

Figure 4:
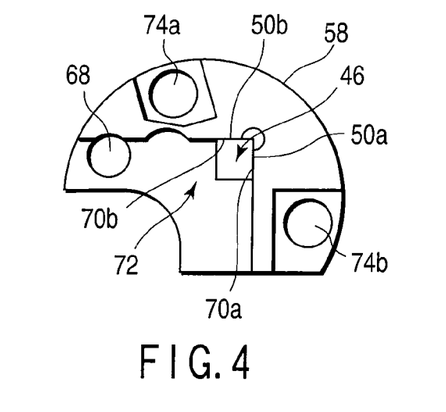
FIG. 4 is a schematic diagram showing the positioning of an LED and a light guide holding member of the embodiment of the present invention.
Figure 5:
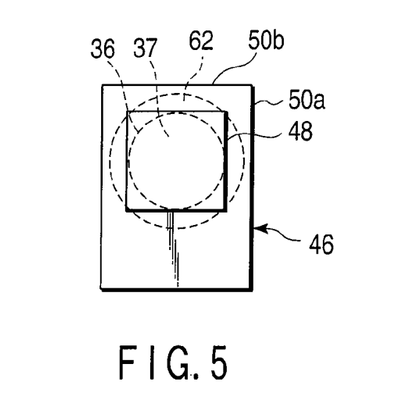
FIG. 5 is a schematic diagram showing the positioning of the LED and a light guide of the embodiment of the present invention.

In the light guide holding member 58, a protruding shape in the axial direction is formed on the end surface portion on the LED substrate 52 side. First and second wall surfaces 70a, 70b forming a positioning portion are formed of the side surfaces of the protruding shape. The first and second wall surfaces 70a, 70b are substantially parallel to the axial direction and orthogonal to each other, and are to be abutted on the first and second side surfaces 50a, 50b of the LED 46, respectively. As shown in FIG. 4, abutting the first and second wall surfaces 70a, 70b on the first and second side surfaces 50a, 50b, respectively, determines uniquely the relative positions of the light guide holding member 58 and the LED 46. When the light guide holding member 58 and the LED 46 are mutually positioned, an opening portion of the light guide insertion hole 60 of the light guide holding member 58 is arranged so as to face the top surface of the LED 46, the proximal end portion of the light guide connecter 62 inserted into the light guide insertion hole 60 is abutted on the top surface of the LED 46, and the proximal end surface of the light guide 36 is arranged so as to face the light emission surface 48 of the LED 46. Here, the proximal end surface of the light guide 36 forms an incidence surface 37 as an incident portion wherein the illuminative light is to enter the incident portion. Furthermore, in order to minimize the loss of a light quantity when the illuminative light enters the incidence surface 37 from the light emission surface 48, as shown in FIG. 5, the incidence surface 37 and the light emission surface 48 are arranged so that the centers thereof match with each other.

Figure 6:
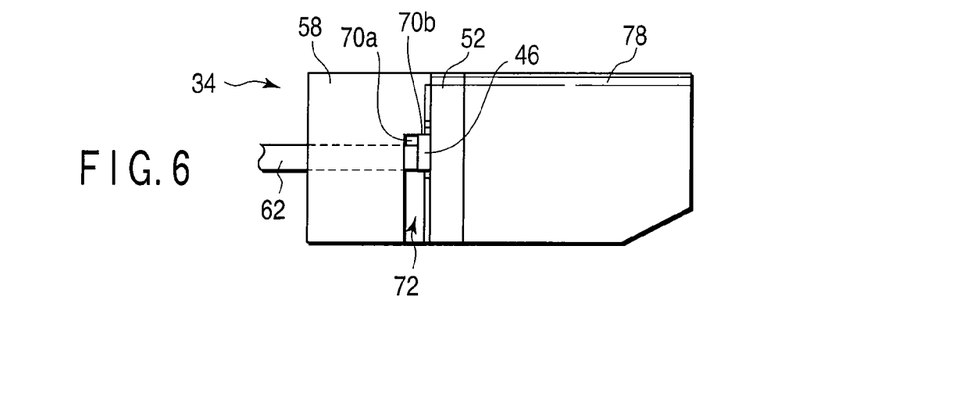
FIG. 6 is another side view showing the LED unit of the embodiment of the present invention.

Furthermore, in the light guide holding member 58, an open portion 72 forming an observing portion is formed so as to open outwardly from the first and second side surfaces 50a, 50b. As shown in FIG. 6, when the end surface of the protruding shape of the light guide holding member 58 is abutted on the LED substrate 52 and the first and second side surfaces 50a, 50b of the LED 46 are arranged in the vicinity of the first and second wall surfaces 70a, 70b of the light guide holding member 58, respectively, an abutment states between the first and second wall surfaces 70a, 70b and the first and second side surfaces 50a, 50b is observable via the open portion 72, respectively. It is to be noted that in the present embodiment, the integral open portion 72 is used, but two separate open portions may be used in observing an abutment state between the first wall surface 70a and the first side surface 50a and observing an abutment state between the second wall surface 70b and the second side surface 50b.

An adjustment joining mechanism of the light source unit 34 will hereinafter be described.

As shown in FIGS. 2, 3A and 3B, in the outer peripheral portion of the light guide holding member 58, first and second groove portions 73a, 73b is extended in the axial direction from the end surface opposite to the LED substrate 52 to a position before the end surface on the LED substrate 52 side. First and second holding member insertion holes 74a, 74b are pierced from end surfaces 75a, 75b of the first and second groove portions 73a, 73b to the end surface on the LED substrate 52 side. First and second joining screws 76a, 76b are to be inserted through the first and second holding member insertion holes 74a, 74b, and heads of the first and second joining screws 76a, 76b are to be engaged with the end surfaces 75a, 75b of the first and second groove portions 73a, 73b.

Moreover, first and second substrate insertion holes 56a, 56b are formed through the LED substrate 52 orthogonal to the LED substrate 52 and the first and second joining screws 76a, 76b are to be inserted through the first and second substrate insertion holes 56a, 56b, respectively.

An LED substrate sandwiching member 78 as a substrate holding member sandwiching member is arranged on the back surface side of the LED substrate 52. First and second sandwiching screw holes 80a, 80b are bored in the axial direction on the LED substrate 52 side end surface of the LED substrate sandwiching member 78 and the first and second joining screws 76a, 76b are to be screwed into the first and second sandwiching screw holes 80a, 80b.

Inserting the first and second joining screws 76a, 76b through the first and second holding member insertion holes 74a, 74b of the light guide holding member 58 and the first and second substrate insertion holes 56a, 56b of the LED substrate 52, respectively, and screwing the first and second joining screws 76a, 76b into the first and second sandwiching screw holes 80a, 80b of the LED substrate sandwiching member 78, respectively, enable to sandwich the LED substrate 52 between the light guide holding member 58 and the LED substrate sandwiching member 78. That is, the end surface of the protruding shape of the light guide holding member 58 is to be brought into face contact with the mounting surface of the LED substrate 52, and the end surface of the LED substrate sandwiching member 78 is to be brought into face contact with the back surface of the LED substrate 52. Furthermore, the inner diameter of the first and second holding member insertion holes 74a, 74b and the inner diameter of the first and second substrate insertion holes 56a, 56b is larger than the outer diameter of the first and second joining screws 76a, 76b and so constant play is formed. In consequence, when joining the light guide holding member 58, the LED substrate 52 and the LED substrate sandwiching member 78, it is enabled to adjust the relative positions of the light guide holding member 58, the LED substrate 52 and the LED substrate sandwiching member 78 in a direction orthogonal to the axial direction.

It is to be noted that a cable 54 for transmitting an electric signal or the like to the LED 46 is extended from the LED substrate 52. Furthermore, a cable insertion hole 68 is formed through the light guide holding member 58 in the axial direction and the cable 54 extended from the LED substrate 52 is to be inserted through the cable insertion hole 68.

Figure 7:
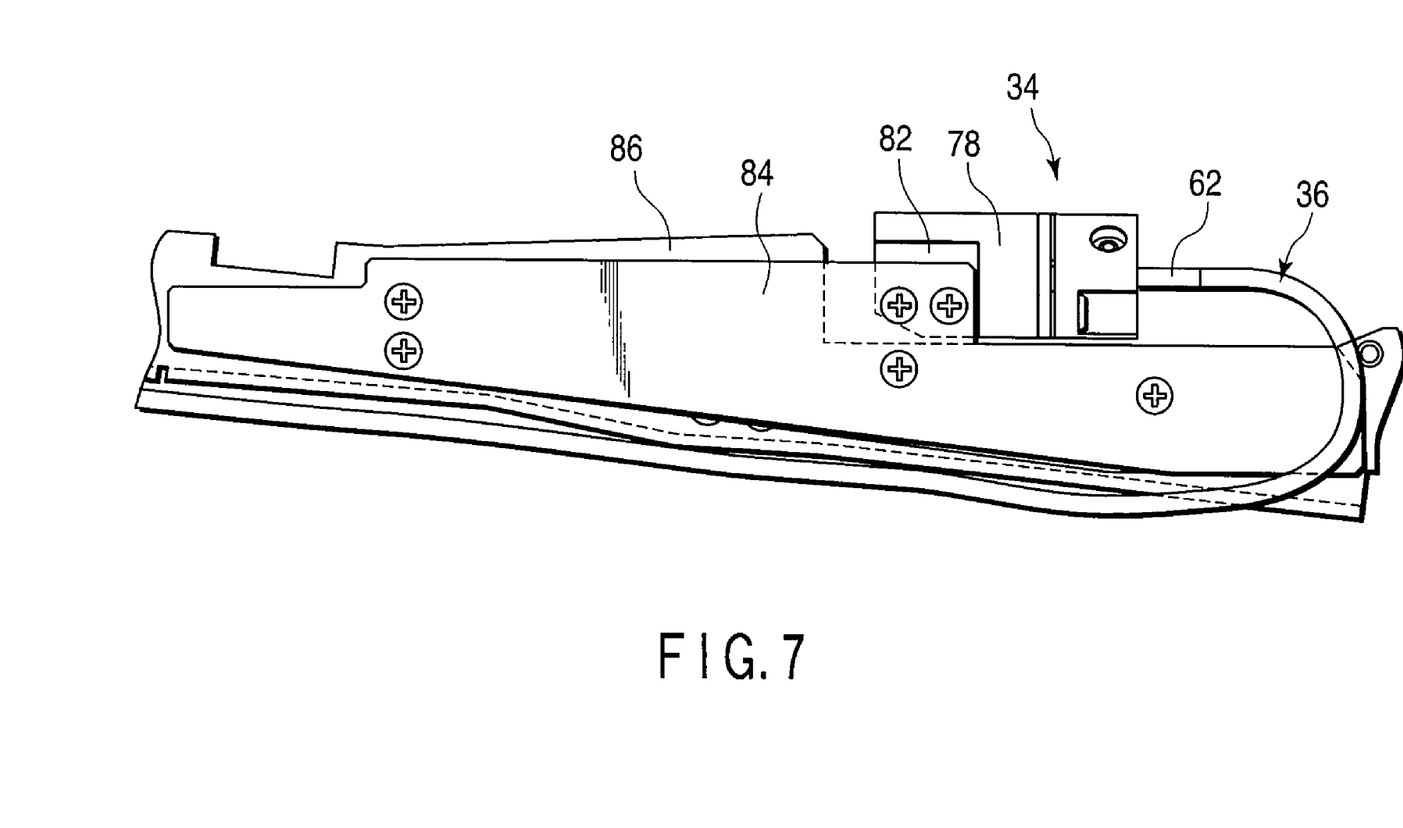
FIG. 7 is a side view showing the inner part of a grasping portion of the embodiment of the present invention.

A mounting mechanism of the LED unit 34 in the grasping portion 18 of the endoscope will hereinafter be described.

As shown in FIG. 7, a planar portion 82 is formed substantially parallel to the axial direction on the outer peripheral portion of the LED substrate sandwiching member 78 of the LED unit 34. The planar portion 82 of the LED substrate sandwiching member 78 is brought into face contact with a radiator frame 84, and fixed thereto with screws. The radiator frame 84 is brought into face contact with a grasping portion frame 86 arranged in the grasping portion, and fixed thereto with screws.

The LED unit 34 is arranged so that the LED substrate sandwiching member 78 is disposed on the distal end side and the light guide holding member 58 is disposed on the proximal end side. The light guide 36 is protruded from the LED unit 34 to the proximal end side, is then gradually turned back and extended along the outer side of the grasping portion frame 86 from the proximal end side to the distal end side, and is introduced into the insertion portion. Thus, even when the light guide 36 has an extra length, it is enabled to receive the light guide 36 in the grasping portion without load of any excessive stress.

Next, an assembly method of the LED unit 34 will be described.

When assembling the LED unit 34, the cable 54 extended from the LED substrate 52 is inserted through the cable insertion hole 68 of the light guide holding member 58. Subsequently, the first and second joining screws 76a, 76b are inserted through the first and second holding member insertion holes 74a, 74b of the light guide holding member 58 and the first and second substrate insertion holes 56a, 56b of the LED substrate 52, respectively, and are screwed into the first and second sandwiching screw holes 80a, 80b of the LED substrate sandwiching member 78, respectively. During this, the relative positions of the light guide holding member 58 and the LED substrate 52 are adjusted with respect to a direction orthogonal to the axial direction, and the first and second wall surfaces 70a, 70b of the light guide holding member 58 are abutted on the first and second side surfaces 50a, 50b of the LED 46, and so the light guide holding member 58 and the LED 46 are positioned. In a state where the first and second wall surfaces 70a, 70b completely abut on the first and second side surfaces 50a, 50b, the first and second joining screws 76a, 76b are sufficiently screwed into the first and second sandwiching screw holes 80a, 80b, and so the LED substrate 52 is securely sandwiched between the light guide holding member 58 and the LED substrate sandwiching member 78. It is to be noted that in a joining operation, it is possible to appropriately adjust the relative position of the LED substrate sandwiching member 78 with respect to the light guide holding member 58 and the LED substrate 52 with respect to the direction orthogonal to the axial direction. As occasion demand, an abutment states between the first and second wall surfaces 70a, 70b of the light guide holding member 58 and the first and second side surfaces 50a, 50b of the LED 46 are confirmed by visual inspection or use of a microscope via the open portion 72 of the light guide holding member 58. Subsequently, the light guide connecter 62 is inserted through the light guide insertion hole 60 of the light guide holding member 58, the proximal end portion of the light guide connecter 62 is abutted on the LED 46, and the light guide connecter 62 is fixed to the light guide holding member 58 with the fixing screw 66. Consequently, the incidence surface 37 of the light guide 36 faces the light emission surface 48 of the LED 46, and the center of the incidence surface matches that of the light emission surface 48 of the LED 46. Thus, the LED unit 34 is assembled.

Subsequently, a heat release function in the LED unit 34 will be described.

The LED 46 has a high temperature due to light emission. Heat generated in the LED 46 is released to the light guide holding member 58 via the first and second wall surfaces 70a, 70b as a heat release portion of the light guide holding member 58, which is brought into face contact with the first and second side surfaces 50a, 50b of the LED 46, via the light guide connecter 62 from the light emission surface 48, and directly by radiation. Moreover, the heat transmitted from the LED 46 to the LED substrate 52 is released to the light guide holding member 58 via the end surface of the protruding shape of the light guide holding member 58, which is brought into face contact with the mounting surface of the LED substrate 52, and is released to the LED substrate sandwiching member 78 via the end surface of the LED substrate sandwiching member 78, which is brought into face contact with the back surface of the LED substrate 52. The heat transmitted to the LED substrate sandwiching member 78 is further released to the radiator frame 84 and the grasping portion frame 86. Thus, the light guide holding member 58 and the LED substrate sandwiching member 78 also have a heat release function.

Therefore, the LED unit 34 of the present embodiment produces the following effects.

In the LED unit 34 of the present embodiment, just only abutting the first and second side surfaces 50a, 50b of the LED 46 on the first and second wall surfaces 70a, 70b of the light guide holding member 58, respectively, and then joining the light guide holding member 58 and the LED substrate sandwiching member 78 to sandwich the LED substrate 52 therebetween enable correct positioning of the light emission surface 48 of the LED 46 and the incidence surface 37 of the light guide 36 with respect to the direction orthogonal to the light emitting direction of the light emission surface 48. That is, it is enabled to easily and correctly position the light emission surface 48 of the LED 46 and the incidence surface 37 of the light guide 36.

It is to be noted that since the abutment states between the first and second side surfaces 50a, 50b and the first and second wall surfaces 70a, 70b is observable, respectively, through the open portion 72 of the light guide holding member 58, it is enabled to easily and securely abut the first and second side surfaces 50a, 50b on the first and second wall surfaces 70a, 70b, respectively.

Moreover, since the relative positions of the light guide holding member 58, the LED substrate 52 and the LED substrate sandwiching member 78 is adjustable with respect to the direction orthogonal to the axial direction, it is enabled to sufficiently secure an adjustable range with a compact constitution, in particular, as compared with a case where the relative positions of the light guide holding member 58 and the LED substrate sandwiching member 78 or the relative positions of the LED substrate 52 and the LED substrate sandwiching member 78 is not adjustable.

Furthermore, in the LED unit 34, the first and second wall surfaces 70a, 70b of the light guide holding member 58 are brought into face contact with the first and second side surfaces 50a, 50b of the LED 46, the proximal end surface of the light guide connecter 62 is abutted on the top surface of the LED 46, and the end surface of the protruding shape of the light guide holding member 58 and the end surface of the LED substrate sandwiching member 78 are brought into face contact with the LED substrate 52, and so the light guide holding member 58 and the LED substrate sandwiching member 78 is used in releasing the heat from the LED 46. Therefore, the heat release efficiency of the LED 46 is improved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the append portioned claims and their equivalents.

What is claimed is:

1. A light source unit comprising:
   a light source including a light emitting portion;
   a light source holding member holding the light source;
   a light transmission member including an incident portion wherein light from the light emitting portion is to enter the incident portion;
   a light transmission member holding member holding the light transmission member;
   a positioning portion provided on the light transmission member holding member and abutted on the light source to position the light transmission member holding member and the light source to position the incident portion and the light emitting portion; and
   an adjustment joining mechanism configured to join the light transmission member holding member and the light source holding member to each other so as to adjust the relative positions of the light transmission member holding member and the light source holding member, and joining the light transmission member holding member and the light source holding member to each other in a state where the light source and the positioning portion abut on each other.

2. The light source unit according to claim 1,
   wherein the light source includes a side surface and the normal direction of the side surface forms an angle with respect to a light emitting direction of the light emitting portion, and
   the positioning portion includes a wall surface abutting on the side surface.

3. The light source unit according to claim 1,
   wherein the light source includes first and second side surfaces and the normal directions of the first and second side surfaces form angles with respect to a light emitting direction of the light emitting portion and face different directions with respect to each other, and
   the positioning portion includes a first wall surface abutting on the first side surface and a second wall surface abutting on the second side surface.

4. The light source unit according to claim 1,
   wherein the light transmission member holding member includes an observing portion provided in the light transmission member holding member and an abutment state between the light source and the positioning portion is observable through the observing portion.

5. The light source unit according to claim 2,
   wherein the light transmission member holding member includes an open portion extending outwardly from the wall surface in the light transmission member holding member and an abutment state between the side surface and the wall surface is observable through the open portion.

6. The light source unit according to claim 3,
   wherein the light transmission member holding member includes a first open portion extending outwardly from the first wall surface in the light transmission member holding member and a second open portion extending outwardly from the second wall surface in the light transmission member holding member, and an abutment state between the first side surface and the first wall surface is observable through the first open portion and an abutment state between the second side surface and the second wall surface is observable through the second open portion.

7. The light source unit according to claim 1,
   wherein the adjustment joining mechanism includes a light source holding member sandwiching member, and
   the light transmission member holding member and the light source holding member sandwiching member are configured to sandwich the light source holding member so as to adjust the relative positions of the light source holding member with respect to the light transmission member holding member.

8. The light source unit according to claim 7,
   wherein the adjustment joining mechanism is configured to join the light transmission member holding member and the light source holding member sandwiching member to each other so as to adjust the relative positions of the light transmission member holding member and the light source holding member sandwiching member.

9. The light source unit according to claim 1,
   wherein the light transmission member holding member includes a heat release portion to release heat generated in the light source.

10. The light source unit according to claim 9,
    wherein the heat release portion is provided on the positioning portion.

11. The light source unit according to claim 7,
wherein the light source holding member sandwiching member includes a heat release function of releasing heat generated in the light source.

12. An endoscope comprising a light source unit, the light source unit including:
a light source including a light emitting portion;
a light source holding member holding the light source;
a light transmission member including an incident portion wherein light from the light emitting portion is to enter the incident portion;
a light transmission member holding member holding the light transmission member;
a positioning portion provided on the light transmission member holding member and abutted on the light source to position the light transmission member holding member and the light source to position the incident portion and the light emitting portion; and
an adjustment joining mechanism configured to join the light transmission member holding member and the light source holding member to each other so as to adjust the relative positions of the light transmission member holding member and the light source holding member, and joining the light transmission member holding member and the light source holding member to each other in a state where the light source and the positioning portion abut on each other.

* * * * *